(12) United States Patent
Shirai et al.

(10) Patent No.: US 9,593,058 B2
(45) Date of Patent: Mar. 14, 2017

(54) METHOD FOR PRODUCING 1,1-DIBROMO-1-FLUOROETHANE

(71) Applicant: DAIKIN INDUSTRIES, LTD., Osaka (JP)

(72) Inventors: Atsushi Shirai, Osaka (JP); Masatoshi Nose, Osaka (JP); Yosuke Kishikawa, Osaka (JP); Tatsuya Ohtsuka, Osaka (JP); Sumi Ishihara, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 14/915,677

(22) PCT Filed: Sep. 3, 2014

(86) PCT No.: PCT/JP2014/073267
§ 371 (c)(1),
(2) Date: Mar. 1, 2016

(87) PCT Pub. No.: WO2015/033985
PCT Pub. Date: Mar. 12, 2015

(65) Prior Publication Data
US 2016/0221900 A1    Aug. 4, 2016

(30) Foreign Application Priority Data
Sep. 3, 2013 (JP) .................. 2013-182500

(51) Int. Cl.
| | |
|---|---|
| *C07C 17/25* | (2006.01) |
| *C07C 17/20* | (2006.01) |
| *C07C 17/087* | (2006.01) |
| *C07C 19/14* | (2006.01) |
| *C07C 21/18* | (2006.01) |

(52) U.S. Cl.
CPC ............ *C07C 17/25* (2013.01); *C07C 17/087* (2013.01); *C07C 17/208* (2013.01)

(58) Field of Classification Search
CPC .............................. C07C 17/25; C07C 17/087
See application file for complete search history.

(56) References Cited

U.S. PATENT DOCUMENTS 5,777,185 A * 7/1998 Belter ................ C07C 17/21
570/164

FOREIGN PATENT DOCUMENTS

JP    05-331083    12/1993

OTHER PUBLICATIONS

Shimokawa et al. JP 05331083 Abstract, May 1992.*
International Search Report issued Nov. 18, 2014 in International (PCT) Application No. PCT/JP2014/073267.
Amaiz et al., "Preparacion de Ioduros de Alquilo por Reaccion de AlI$_3$ Sobre Los Cloruros", Anales de Quimica, vol. 82, No. 3, (1985), pp. 270-271.

* cited by examiner

*Primary Examiner* — Jafar Parsa
(74) *Attorney, Agent, or Firm* — Wenderoth, Lind & Ponack, L.L.P.

(57) ABSTRACT

An object of the present invention is to provide a production method that makes it possible to produce 1,1-dibromo-1-fluoroethane easily and sustainably.
The present invention provides a method for producing 1,1-dibromo-1-fluoroethane, the method comprising step A of reacting 1,1-dibromoethylene with hydrogen fluoride to obtain 1,1-dibromo-1-fluoroethane.

12 Claims, No Drawings

METHOD FOR PRODUCING 1,1-DIBROMO-1-FLUOROETHANE

TECHNICAL FIELD

The present invention relates to a method for producing 1,1-dibromo-1-fluoroethane.

BACKGROUND ART

Regarding a method for producing 1,1-dibromo-1-fluoroethane in a high yield, Patent Literature 1 discloses a method in which a monofluoroalkane is brominated to prepare a 1,1-dibromo-1-fluoroalkane.

CITATION LIST

Patent Literature

PTL 1: JPH05-331083A

SUMMARY OF INVENTION

Technical Problem

However, with the method disclosed in Patent Literature 1, aqueous hydrofluoric acid is generated in the fluorination step, resulting in significant corrosiveness to the reaction vessel. Moreover, since the bromination step requires an ultrahigh temperature condition of 500 to 700° C. and causes generation of hydrogen bromide and hydrogen fluoride, corrosiveness to the reaction vessel is also significant in this step. Accordingly, the method disclosed in Patent Literature 1 has a disadvantage in easily and sustainably producing 1,1-dibromo-1-fluoroethane.

Therefore, an object of the present invention is to provide a method for easily and sustainably producing 1,1-dibromo-1-fluoroethane.

Solution to Problem

The present inventors conducted extensive research and found that 1,1-dibromo-1-fluoroethane can be produced easily and sustainably by a method for producing 1,1-dibromo-1-fluoroethane, the method comprising step A of reacting 1,1-dibromoethylene with hydrogen fluoride to obtain 1,1-dibromo-1-fluoroethane. The present invention has thus been accomplished.

The present invention includes the following embodiments.

Item 1.

A method for producing 1,1-dibromo-1-fluoroethane, the method comprising step A of reacting 1,1-dibromoethylene with hydrogen fluoride to obtain 1,1-dibromo-1-fluoroethane.

Item 2.

The method according to Item 1, wherein the reaction of step A is performed in the presence of an amine.

Item 3.

The method according to Item 1 or 2, wherein 1,1-dibromoethylene is produced by a production method comprising step B of reacting 1,1,1-trihaloethane with an aluminum halide having one or more bromine atoms to obtain 1,1,1-tribromoethane and step C of dehydrobrominating 1,1,1-tribromoethane using a base to obtain 1,1-dibromoethylene.

Item 4.

The method according to Item 3, wherein the 1,1,1-trihaloethane is 1,1,1-trichloroethane.

Item 5.

A method for producing 1-bromo-1-fluoroethylene, the method comprising step D of dehydrobrominating 1,1-dibromo-1-fluoroethane obtained by the method according to any one of Items 1 to 4 to obtain 1-bromo-1-fluoroethylene.

Advantageous Effects of Invention

The production method of the present invention makes it possible to produce 1,1-dibromo-1-fluoroethane easily and sustainably.

DESCRIPTION OF EMBODIMENTS

The method for producing 1,1-dibromo-1-fluoroethane of the present invention comprises step A of reacting 1,1-dibromoethylene with hydrogen fluoride to obtain 1,1-dibromo-1-fluoroethane.

The 1,1-dibromoethylene used in step A can be produced by a production method comprising step B of reacting 1,1,1-trihaloethane with an aluminum halide having one or more bromine atoms to obtain 1,1,1-tribromoethane and step C of dehydrobrominating 1,1,1-tribromoethane using a base to obtain 1,1-dibromoethylene.

The 1,1-dibromo-1-fluoroethane obtained in step A can be dehydrobrominated to obtain 1-bromo-1-fluoroethylene (step D).

Steps A to D are described in detail below.

Step A

In step A, 1,1-dibromoethylene is reacted with hydrogen fluoride to obtain 1,1-dibromo-1-fluoroethane.

The reaction of step A may be a reaction in a liquid phase or a reaction in a gas phase.

The reaction of step A is preferably a reaction in a liquid phase.

The reaction of step A may be performed in the absence or presence of a solvent. The reaction of step A is preferably performed in the absence of a solvent.

When the reaction of step A is performed in the presence of a solvent, examples of the solvent include alcohol solvents (e.g., methanol, ethanol, n-propanol, isopropanol, and n-BuOH);
ketone solvents (e.g., acetone and methyl ethyl ketone (MEK));
ether solvents (e.g., diethyl ether, tetrahydrofuran (THF), and 1-methoxy-2-(2-methoxyethoxy)ethane (Diglyme));
halogen-containing solvents (e.g., methylene chloride, chloroform, carbon tetrachloride, ethyl chloride, 1,1-dichloroethane, 1,2-dichloroethane, 1-chloropropane, 2-chloropropane, 1-chlorobutane, 2-chlorobutane, 1-chloro-2-methylpropane, 1-chloropentane, 1,1,2-trichloroethane, $CH_3CClF_2$, $CH_3CCl_2F$, $CF_3CF_2CCl_2H$, $CF_2ClCF_2CFHCl$, and like hydrochlorofluoroalkanes; $CF_2ClCFClCF_2CF_3$, $CF_3CFClCFClCF_3$, and like chlorofluoroalkanes; and perfluorocyclobutane, $CF_3CF_2CF_2CF_3$, $CF_3CF_2CF_2CF_2CF_3$, $CF_3CF_2CF_2CF_2CF_2CF_3$, and like perfluoroalkanes);
hydrocarbon solvents (e.g., n-hexane, n-heptane, n-octane, n-nonane, n-decane, cyclohexane, cycloheptane, benzene, toluene, xylene, and mesitylene); and
water.

When the reaction of step A is performed in the presence of a solvent, these solvents may be used singly or in a combination of two or more.

Step A is preferably performed using an autoclave as a reaction vessel.

The amount of the hydrogen fluoride is generally within the range of 0.5 to 60 mol, preferably within the range of 3 to 50 mol, and more preferably within the range of 5 to 40 mol, per mol of 1,1-dibromoethylene.

Step A is performed at a temperature generally within the range of 0 to 200° C., preferably within the range of 5 to 80° C., and more preferably within the range of 5 to 70° C. The temperature can be adjusted by, for example, adjusting the external temperature of the reaction vessel to a predetermined temperature. The internal temperature of the reaction vessel can be regarded as substantially the same as the external temperature.

The reaction time of step A is generally within the range of 1 to 40 hours, preferably within the range of 1 to 24 hours, and more preferably within the range of 1 to 20 hours.

1,1-dibromo-1-fluoroethane can be obtained by, for example, lowering the temperature of the reaction system by cooling after the reaction time has passed, subsequently adding water to the reaction liquid, and then performing liquid separation.

In a preferred embodiment of the present invention, a hydrogen fluoride layer and a 1,1-dibromo-1-fluoroethane layer can be separated by means of liquid separation after cooling to obtain 1,1-dibromo-1-fluoroethane and collect hydrogen fluoride.

In another preferred embodiment of the present invention, hydrogen fluoride can be distilled off under reduced pressure after cooling to obtain 1,1-dibromo-1-fluoroethane and collect the hydrogen fluoride.

The method for cooling may be, for example, cooling by leaving at room temperature, cooling with ice water, cooling with a chiller, or cooling with dry ice.

The obtained 1,1-dibromo-1-fluoroethane may be further purified by a known purification method, such as solvent extraction, drying, filtration, distillation, concentration, or a combination of these, as necessary.

The 1,1-dibromoethylene used in step A can be preferably produced by, for example, a method comprising step B of reacting 1,1,1-trihaloethane with an aluminum halide having one or more bromine atoms to obtain 1,1,1-tribromoethane and step C of dehydrobrominating 1,1,1-tribromoethane using a base to obtain 1,1-dibromoethylene.

The 1,1-dibromoethylene used in step A may be present with a polymerization inhibitor before, during, or both before and during the reaction of step A. The polymerization inhibitor may be, for example, an amine described below as an example of the amine used as necessary in step A. The amount of the polymerization inhibitor is generally within the range of 0.01 to 15% (w/w), preferably within the range of 0.01 to 10% (w/w), and more preferably within the range of 0.01 to 7% (w/w), relative to 1,1-dibromoethylene.

The 1,1-dibromoethylene used in step A can also be produced by a known method, specifically by dehydrobromination reaction of 1,1,2-tribromoethane (J. Am. Chem. Soc., 1985, 107, 2023-2032).

The hydrogen fluoride used in step A is commercially available. The hydrogen fluoride used in step A may be, for example, in the form of anhydrous hydrogen fluoride (i.e., anhydrous hydrofluoric acid) or aqueous hydrofluoric acid (i.e., aqueous solution of hydrogen fluoride). Further, the hydrogen fluoride used in step A may be in the gaseous form. Hydrogen fluoride in the gaseous form may be a mixture of HF (hydrogen fluoride) and a polymer of HF.

The reaction of step A is preferably performed in the presence of an amine.

In the reaction, some or all of the hydrogen fluoride may form a complex with the amine.

This improves the yield of the desired product.

Examples of amines include aliphatic primary amines, aliphatic secondary amines, aliphatic tertiary amines, alicyclic secondary amines, alicyclic tertiary amines, aromatic amines, heterocyclic amines, polymer-supported amine compounds and like amine compounds, and the like.

Examples of aliphatic primary amines include methylamine, ethylamine, propylamine, butylamine, pentylamine, hexylamine, cyclohexylamine, and ethylenediamine.

Examples of aliphatic secondary amines include dimethylamine, diethylamine, dipropylamine, dibutylamine, dipentylamine, dihexylamine, and dicyclohexylamine.

Examples of aliphatic tertiary amines include trimethylamine, triethylamine, diisopropylethylamine, tributylamine, and N,N,N',N'-tetramethylethylenediamine.

Examples of alicyclic secondary amines include piperidine, piperazine, pyrrolidine, and morpholine.

Examples of alicyclic tertiary amines include N-methylpiperazine, N-methylpyrrolidine, 5-diazabicyclo[4.3.0]nonan-5-ene, and 1,4-diazabicyclo[2.2.2]octane.

Examples of aromatic amines include aniline, methylaniline, dimethylaniline, N,N-dimethylaniline, haloaniline, and nitroaniline.

Examples of heterocyclic amines include pyridine, pyrimidine, piperazine, quinoline, phenothiazine, melamine, and imidazole.

Examples of polymer-supported amine compounds include polyallylamine and polyvinylpyridine.

Of these, preferred are, for example, diisopropylethylamine, tributylamine, triethylamine, pyridine, melamine, phenothiazine, and the like.

These amines may be used singly or in a combination of two or more.

The amount of the amine is preferably within the range of 1 to 100% (w/w), more preferably within the range of 1 to 50% (w/w), even more preferably within the range of 1 to 30% (w/w), and still even more preferably within the range of 3 to 30% (w/w), relative to the hydrogen fluoride.

In step A, for example, a mixture of an amine and hydrogen fluoride may be added to 1,1-dibromoethylene; hydrogen fluoride and an amine may be individually added to 1,1-dibromoethylene; or a mixture of an amine and hydrogen fluoride, and hydrogen fluoride may be individually added to 1,1-dibromoethylene. The mixture of an amine and hydrogen fluoride may be a complex of an amine and hydrogen fluoride. The amine may be an amine as the polymerization inhibitor, mentioned above, which may be present with 1,1-dibromoethylene.

Step B

In step B, 1,1,1-trihaloethane is reacted with an aluminum halide having one or more bromine atoms to obtain 1,1,1-tribromoethane.

The 1,1,1-trihaloethane and aluminum halide having one or more bromine atoms used in step B are both known compounds, and can be produced by a known method or are commercially available.

Examples of aluminum halides having one or more bromine atoms include $AlBrCl_2$, $AlBr_2Cl$, $AlBrF_2$, $AlBr_2F$, $AlBrClF$, and $AlBr_3$ (aluminum tribromide). These aluminum halides having one or more bromine atoms may be used singly or in a combination of two or more. The aluminum halide having one or more bromine atoms is preferably $AlBrCl_2$, $AlBr_2Cl$, or $AlBr_3$, and more preferably $AlBr_3$.

The 1,1,1-trihaloethane is represented by the general formula: $CH_3\text{—}CBr_xCl_yF_z$ (wherein x represents an integer of 0 to 2, y represents an integer of 0 to 3, and z represents an integer of 0 to 3, with the proviso that the sum of x, y, and z is 3).

The 1,1,1-trihaloethane is, for example, preferably 1,1,1-trichloroethane, 1,1-dichloro-1-bromoethane, or 1-chloro-1,1-dibromoethane, and more preferably 1,1,1-trichloroethane.

The amount of the aluminum halide having one or more bromine atoms is generally 0.3 to 3 mol, preferably 0.3 to 2 mol, and more preferably 0.3 to 1.5 mol, per mol of the 1,1,1-trihaloethane.

Step B is preferably performed in the presence of a solvent.

Examples of solvents include dibromomethane, bromoethane, 1,1-dibromoethane, diethyl ether, dibutyl ether, heptane, hexane, 1,2-dibromoethane, and the like. The solvent is preferably a bromine-containing solvent (e.g., dibromomethane, bromoethane, 1,1-dibromoethane, and 1,2-dibromoethane). These solvents may be used singly or in combination.

The amount of the solvent used is not particularly limited insofar as some or all of the starting materials are dissolved at the reaction temperature. For example, the solvent may be used in an amount of 1 to 30 parts by weight per part by weight of the 1,1,1-trihaloethane.

Step B is performed at a temperature generally within the range of −30 to 100° C., preferably within the range of −20 to 50° C., and more preferably within the range of −5 to 20° C.

The reaction time of step B is generally within the range of 0.1 to 10 hours, preferably within the range of 0.1 to 5 hours, and more preferably within the range of 0.1 to 2 hours.

The obtained 1,1,1-tribromoethane may be subjected to step C as is, or may be further purified by a known purification method, such as solvent extraction, drying, filtration, distillation, concentration, or a combination of these, as necessary.

The method of step B is superior to a known method (a method of metylating bromoform using one or more equivalents of n-butyllithium and diisopropylamine at a ultralow temperature (J. Am. Chem. Soc., 2010, 132, pp. 773-776)) in that a large amount of a base, which is expensive, is not required and in that the temperature condition is mild.

Step C

In step C, 1,1,1-tribromoethane is dehydrobrominated using a base to obtain 1,1-dibromoethylene.

Examples of the base used in step C include inorganic bases, such as sodium hydroxide, potassium hydroxide, cesium hydroxide, potassium carbonate, sodium carbonate, sodium hydrogencarbonate, sodium methylate, sodium ethylate, and potassium t-butylate; and organic bases, such as trimethylamine, triethylamine, diisopropylethylamine, tributylamine, aniline, methylaniline, dimethylaniline, N,N-dimethylaniline, and like amines. These bases may be used singly or in combination. For example, an amine and an inorganic base may be used in combination in a catalytic amount.

The amount of the base is generally within the range of 1 to 20 equivalents, preferably within the range of 1 to 10 equivalents, and more preferably within the range of 1 to 5 equivalents, relative to 1,1,1-tribromoethane.

Step C is preferably performed in the presence of a solvent.

Examples of solvents include protic solvents, such as water, methanol, ethanol, and ethylene glycol; aprotic solvents, such as tetrahydrofuran, acetone, dioxane, diglyme, acetonitrile, methylene chloride, and N,N-dimethylformamide; and the like. These solvents may be used singly or in combination.

The amount of the solvent used is not particularly limited insofar as some or all of the starting materials are dissolved at the reaction temperature. For example, the solvent may be used in an amount of 1 to 30 parts by weight per part by weight of 1,1,1-tribromoethane.

Step C is performed at a temperature generally within the range of 0 to 100° C., preferably within the range of 20 to 80° C., and more preferably within the range of 20 to 60° C.

The reaction time of step C is generally within the range of 1 to 24 hours, preferably within the range of 1 to 10 hours, and more preferably within the range of 1 to 5 hours.

The obtained 1,1-dibromoethylene may be subjected to step A as is, or may be further purified by a known purification method, such as solvent extraction, drying, filtration, distillation, concentration, or a combination of these, as necessary.

Step D

In step D, 1,1-dibromo-1-fluoroethane obtained in step A is dehydrobrominated to obtain 1-bromo-1-fluoroethylene. The dehydrobromination of step D can be performed, for example, using a base or by thermal decomposition. The dehydrobromination of step D is preferably dehydrobromination performed using a base.

The 1,1-dibromo-1-fluoroethane obtained in step A may be used in step D as is, or may be used after isolation and purification. The isolation and purification can be performed by, for example, addition of water and liquid separation.

Examples of the base used in step D include inorganic bases, such as sodium hydroxide, potassium hydroxide, cesium hydroxide, potassium carbonate, sodium carbonate, sodium hydrogencarbonate, sodium methylate, sodium ethylate, and potassium t-butylate; organic bases, such as trimethylamine, triethylamine, diisopropylethylamine, tributylamine, aniline, methylaniline, dimethylaniline, N,N-dimethylaniline, DBU (diazabicycloundecene) and like amines; and the like. These bases can be used singly or in combination.

The amount of the base is generally within the range of 0.8 to 10 equivalents, preferably within the range of 0.8 to 5 equivalents, and more preferably within the range of 0.8 to 3 equivalents, relative to 1,1-dibromo-1-fluoroethane.

The dehydrobromination performed using a base is carried out at a temperature generally within the range of 10 to 100° C., preferably within the range of 30 to 70° C., and more preferably within the range of 60 to 65° C.

The reaction time of the dehydrobromination performed using a base is generally within the range of 1 to 10 hours, preferably within the range of 2 to 7 hours, and more preferably within the range of 3 to 4 hours.

The thermal decomposition is preferably flow-type gas-phase thermal decomposition. The thermal decomposition is performed at a temperature generally within the range of 300 to 1000° C., preferably within the range of 400 to 900° C., and more preferably within the range of 450 to 600° C. The pressure during the reaction is not particularly limited insofar as the starting material can be present in a gaseous state. Any pressure, i.e., normal pressure, increased pressure, or reduced pressure, may be used. Specifically, the production method of the present invention may be performed under reduced pressure or atmospheric pressure (0.1 MPa), or may also be performed under increased pressure insofar as the starting material does not turn into a liquid. The thermal decomposition time is generally within the range of 0.1 seconds to 1 minute.

The obtained 1,1-dibromo-1-fluoroethane may be purified by a known purification method, such as solvent extraction, drying, filtration, distillation, concentration, or a combination of these, as necessary.

EXAMPLES

Examples are given below to illustrate the present invention in more detail; however, the present invention is not limited to these Examples.

In the Examples described below, gas chromatography (GC) was performed according to the following GC conditions.
GC Conditions
GC apparatus: Shimadzu GC-2010
Column: J&W DB-5MS (0.25 μm, 60 m, 0.25 mmID)
Column oven: 40° C. (5 min)→temperature rising (5° C./min)→200° C. (3 min)
Temperature of vaporizing chamber: 150° C.

Example 1

Step B

Dibromomethane (2 ml) and 1,1,1-trichloroethane (200 mg, 1.5 mmol) were placed in a recovery flask under nitrogen atmosphere. Under ice cooling, aluminum tribromide (439 mg, 1.65 mmol) was added thereto, and the mixture was stirred for 1 hour. Ice water was added to the reaction system, followed by liquid separation, thereby obtaining 1,1,1-tribromoethane (GC area: 55%) and 1-chloro-1,1-dibromoethane (GC area: 5%).

Example 2

Step C

Ethanol (5 ml), 1,1,1-tribromoethane obtained in Example 1 (1.0 g), and sodium hydroxide (150 mg, 3.75 mmol) were placed in an autoclave. After the mixture was heated to 60 to 65° C., a reaction was carried out at the same temperature for 3 to 4 hours, and the reaction vessel was cooled with ice water. Toluene and water were added to the reaction system, followed by liquid separation, thereby obtaining 1,1-dibromoethylene (GC area: 99%).

Example 3

Step A

A 50-cc autoclave was used as a reaction vessel. Hydrogen fluoride (3.1 g, 155 mmol) was added to 1,1-dibromoethylene (5.0 g, 26.9 mmol) obtained in Example 2. A reaction was carried out at an external temperature within the range of 65 to 70° C. for 18 hours, and the reaction vessel was cooled with ice water. Water was added to the reaction mixture, followed by liquid separation, thereby obtaining 1,1-dibromo-1-fluoroethane (GC area: 75.9%).

Example 4

Step D

Sodium hydroxide (41.2 mg, 1.03 mmol) was dissolved in ethanol, and the mixture was heated to 60 to 65° C. 100 ml (211.4 g, 1.03 mol) of 1,1-dibromo-1-fluoroethane obtained in Example 3 was added dropwise thereto with stirring over 45 minutes. After the completion of the dropwise addition, a reaction was carried out at the same temperature for 3 to 4 hours. The obtained gas (1-bromo-1-fluoroethylene) was collected using dry ice acetone (GC area: 99%).

Example 5

Step A

A 50-cc autoclave was used as a reaction vessel. Pyridine-nHF (1.5 g, containing 70% (w/w) HF) and hydrogen fluoride (3 g, 150 mmol) were added to 1,1-dibromoethylene (1.254 g, 6.75 mmol). A reaction was performed at an external temperature of 30° C. for 20 hours, and the reaction vessel was cooled with ice water. Water was added to the reaction mixture, followed by liquid separation, thereby obtaining 1,1-dibromo-1-fluoroethane (GC area: 93%).

Example 6

Step A

A 50-cc autoclave was used as a reaction vessel. Melamine (0.33 g, 2.62 mmol) and hydrogen fluoride (3 g, 150 mmol) were added to 1,1-dibromoethylene (929 mg, 5 mmol). A reaction was performed at an external temperature of 30° C. for 20 hours, and the reaction vessel was cooled with ice water. Water was added to the reaction mixture, followed by liquid separation, thereby obtaining 1,1-dibromo-1-fluoroethane (GC area: 93%).

Example 7

Step A

A 50-cc autoclave was used as a reaction vessel. $Et_3N$-5HF (750 mg) and hydrogen fluoride (3 g, 150 mmol) were added to 1,1-dibromoethylene (1.046 g, 5.63 mmol). A reaction was carried out at an external temperature of 30° C. for 20 hours, and the reaction vessel was cooled with ice water. Water was added to the reaction mixture, followed by liquid separation, thereby obtaining 1,1-dibromo-1-fluoroethane (GC area: 91%).

Example 8

Step A

A 300-cc autoclave was used as a reaction vessel. Pyridine-nHF (18 g, containing 70% (w/w) HF) and hydrogen fluoride (37.77 g, 755.4 mol) were added to 1,1-dibromoethylene (15 g, 80.7 mmol). A reaction was carried out at an external temperature of 30° C. for 20 hours, and the reaction vessel was cooled with ice water. Water was added to the reaction mixture, followed by liquid separation, thereby obtaining an organic layer. The organic layer was neutralized with basic water, followed by liquid separation, thereby obtaining 1,1-dibromo-1-fluoroethane (13.2 g, 80% yield).

INDUSTRIAL APPLICABILITY

The present invention makes it possible to produce 1,1-dibromo-1-fluoroethane easily and sustainably. 1,1-dibromo-1-fluoroethane can be used as synthetic intermediates of pharmaceuticals (e.g., antibiotics), synthetic intermediates for sheath materials of optical fibers, synthetic intermediates of coating materials, synthetic intermediates of semiconductor resist materials, and monomers of functional polymers.

The invention claimed is:

1. A method for producing 1,1-dibromo-1-fluoroethane, the method comprising step A of reacting 1,1-dibromoethylene with hydrogen fluoride to obtain 1,1-dibromo-1-fluoroethane.

2. The method according to claim 1, wherein the reaction of step A is performed in the presence of an amine.

3. The method according to claim 1, wherein 1,1-dibromoethylene is produced by a production method comprising step B of reacting 1,1,1-trihaloethane with an aluminum halide having one or more bromine atoms to obtain 1,1,1-tribromoethane and step C of dehydrobrominating 1,1,1-tribromoethane using a base to obtain 1,1-dibromoethylene.

4. The method according to claim 3, wherein 1,1,1-trihaloethane is 1,1,1-trichloroethane.

5. A method for producing 1-bromo-1-fluoroethylene, the method comprising step D of dehydrobrominating 1,1-dibromo-1-fluoroethane obtained by the method according to claim 1 to obtain 1-bromo-1-fluoroethylene.

6. The method according to claim 2, wherein 1,1-dibromoethylene is produced by a production method comprising step B of reacting 1,1,1-trihaloethane with an aluminum halide having one or more bromine atoms to obtain 1,1,1-tribromoethane and step C of dehydrobrominating 1,1,1-tribromoethane using a base to obtain 1,1-dibromoethylene.

7. The method according to claim 6, wherein 1,1,1-trihaloethane is 1,1,1-trichloroethane.

8. A method for producing 1-bromo-1-fluoroethylene, the method comprising step D of dehydrobrominating 1,1-dibromo-1-fluoroethane obtained by the method according to claim 2 to obtain 1-bromo-1-fluoroethylene.

9. A method for producing 1-bromo-1-fluoroethylene, the method comprising step D of dehydrobrominating 1,1-dibromo-1-fluoroethane obtained by the method according to claim 3 to obtain 1-bromo-1-fluoroethylene.

10. A method for producing 1-bromo-1-fluoroethylene, the method comprising step D of dehydrobrominating 1,1-dibromo-1-fluoroethane obtained by the method according to claim 6 to obtain 1-bromo-1-fluoroethylene.

11. A method for producing 1-bromo-1-fluoroethylene, the method comprising step D of dehydrobrominating 1,1-dibromo-1-fluoroethane obtained by the method according to claim 4 to obtain 1-bromo-1-fluoroethylene.

12. A method for producing 1-bromo-1-fluoroethylene, the method comprising step D of dehydrobrominating 1,1-dibromo-1-fluoroethane obtained by the method according to claim 7 to obtain 1-bromo-1-fluoroethylene.

* * * * *